Figure 1A:
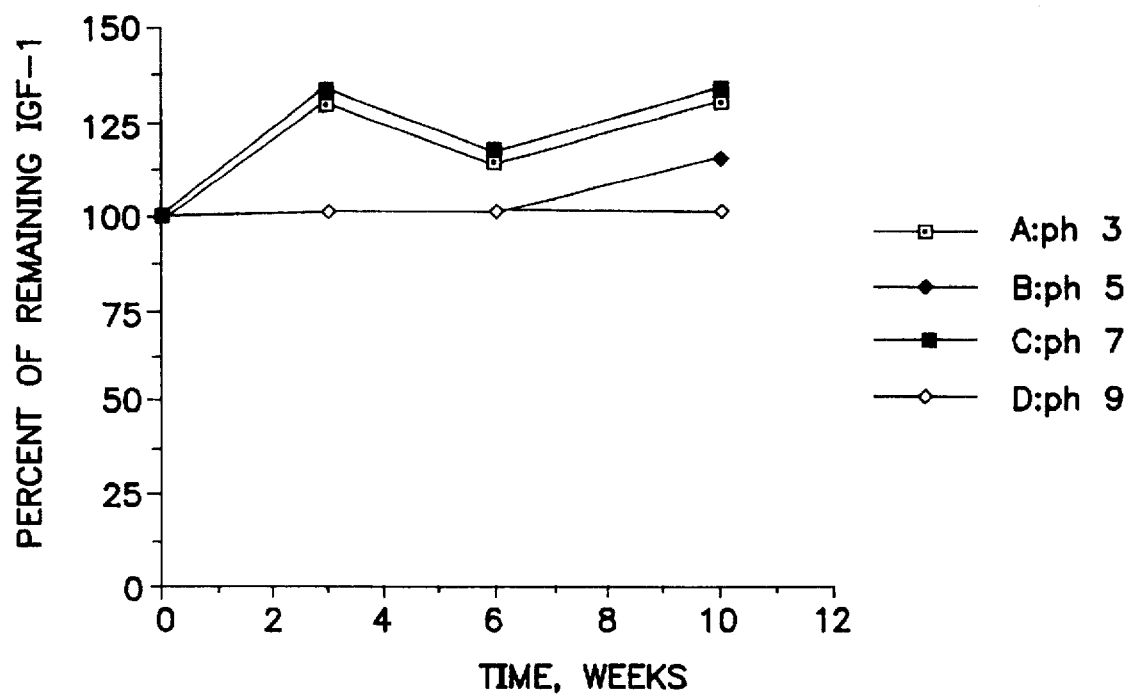

United States Patent [19]

Florin-Robertsson et al.

[11] Patent Number: 5,783,559
[45] Date of Patent: Jul. 21, 1998

US005783559A

[54] SOLUTION CONTAINING IGF-1

[75] Inventors: Ebba Florin-Robertsson, Stockholm; Jonas Fransson, Uppsala; Diane Moore, Upplands Väsby, all of Sweden

[73] Assignee: Pharmacia & Upjohn Aktiebolag, Stockholm, Sweden

[21] Appl. No.: 491,902

[22] PCT Filed: Jan. 10, 1994

[86] PCT No.: PCT/SE94/00010

§ 371 Date: Oct. 16, 1995

§ 102(e) Date: Oct. 16, 1995

[87] PCT Pub. No.: WO94/15584

PCT Pub. Date: Jul. 21, 1994

[30] Foreign Application Priority Data

Jan. 15, 1993 [SE] Sweden .................... 9300105

[51] Int. Cl.$^6$ .................... A61K 38/08; A61K 38/22
[52] U.S. Cl. .................... 514/12; 514/21
[58] Field of Search .................... 514/12, 21

[56] References Cited

U.S. PATENT DOCUMENTS 4,853,224 8/1989 Wong .................... 424/427

FOREIGN PATENT DOCUMENTS 0528313 2/1993 European Pat. Off. .
3939346 6/1991 Germany .
9118621 12/1991 WIPO .

*Primary Examiner*—Cecilia J. Tsang
*Assistant Examiner*—P. Lynn Touzeau
*Attorney, Agent, or Firm*—Pollock, Vande Sande & Priddy

[57] ABSTRACT

The invention relates to solutions containing IGF-1 or any functional analogue thereof in which pH is 5.5 to 6.5, preferably 5.7 to 6.2. The amount of phosphate as buffer substance should be in a concentration of less than 50 mmol/L Preferably the formulation is an aqueous solution of IGF-1 and phosphate as buffer substance in a concentration of 5 to 50 mmole or more preferably 5–20 mmol/L, e.g. 10 mmol/L. The solution should be isotonic. The solution gives a reduced pain upon subcutaneous injection. The invention also relates to a process for preparation of the formulation by mixing IGF-1 or any functional analogue thereof with a buffer substance giving pH 5.5 to 6.5 and an isotonic agent. It also relates to a method for treatment of a patient in need of IGF-1 or any functional analogue thereof by administering the claimed formulation.

13 Claims, 2 Drawing Sheets

SOLUTION CONTAINING IGF-1

The present invention relates to a stable solution containing Insulin-like Growth factor I (IGF-1) in a phosphate buffer in an amount of 50 mmol or less, giving a pH of 5.5 to 6.5, which is isotonic and suitable for injection.

INTRODUCTION

Insulin-like Growth Factor I (IGF-1) is a peptide present in plasma and other body fluids as well as many cells/tissues. It comprises 70 amino acids, including 3 disulphide bonds, and can stimulate proliferation of a wide range of cell types and it mediates some of the effects of growth hormone. Human IGF-1 has been purified from plasma and its complete amino acid sequence is established. (Rinderknecht E et al. "The amino acid sequence of human insulin-like growth factor I and its structural homology with proinsulin" J. Biol. Chem 253; 2769–76, 1978) Sequences with extensive homologies to human IGF-1 are present in IGF-1 purified from plasma of other species.

It has both systemic and local effects and appears mostly associated with different specific binding proteins, four of which have been sequenced and are termed IGFBP1, IGFBP2, IGFBP3 and IGFBP4. These appear to modulate the biological functions and availability of IGF-1 in both a positive and negative manner. Analogues with changed affinities for the binding proteins have been produced and changes of biological activities related to sequence variation have been found. IGF-1 appears to act mainly by interactions with the IGF-type 1 receptor exposed on the outer surface of plasma membranes in many different cell types. However, binding to IGF type 2- and insulin receptors also seems to be of importance.

Because of the scarcity of purified plasma IGF-1 there was a great necessity to develop methodology for the commercial scale production of IGF-1. Nowdays, such large scale production can readily be achieved by using recombinant DNA techniques.

As a result of studies with preparations of recombinant DNA IGF-1 it has been demonstrated that it promotes skeletal growth and skeletal muscle protein synthesis. IGF-1 has been shown to act both as an endocrine factor as well as a paracrine/autocrine factor. (Skottner et al, Endocrinology, Vol.124, No 5, 1989 and Cook et al, J Clin Invest 81; 206–212; 1988)

Moreover, IGF-1 is also effective for the treatment or prevention of catabolic states in patients (Swedish patent application SE 9002731-9) and improves the regeneration of transected peripheral nerves (EP 0 308 386). It has previously been demonstrated in vitro that IGF-1 also can promote actin synthesis in myocytes in culture (Florini, J R, Muscle and Nerve 10 (1987) 577–598 and contractility of neonatal rat cardiocytes in vitro (Vetter, U et al, Basic Res. Cardiol. 83 (1988)647–654).

The stability of proteins is generally a problem in the pharmaceutical industry.

A formulation with a low amount of protein will generally lose activity during purification, sterile manufacturing, storage and during the administration.

It has often been solved by drying of the protein in different drying processes, such as freeze-drying. The protein has thereafter been distributed and stored in dried form. The patient necessarily has to reconstitute the dried protein in a solvent before use, which of course is a disadvantage and is an inconvenience for the patient. For a patient, who needs daily injections of IGF-1, and especially when the patient is a child, it is of importance that the product is easy to handle, to dose and inject. The reconstitution of a freeze-dried product demands prudence and carefulness and should therefore preferably be avoided.

The freeze-drying process is also a costly and time consuming process step, and it would be of great advantage if this step could be avoided, when preparing a commercial product of a protein.

Another possibility is to add human albumin, which generally reduces the activity loss of the active protein considerably. If the protein is freeze-dried, human albumin functions as a general stabilizer during the purification, sterile manufacture and freeze-drying. It is, however, not desirable to add any substance derived from blood, because of a risk of virus contamination of plasma, unless it is absolutely necessary.

It would facilitate the use of a pharmaceutical protein if it can be produced and distributed as a stable solution with a prolonged storage life to the patient, who could inject the medicament directly without reconstitution.

Several solutions have been proposed for the stabilization of different proteins:

EP 35 204 (Cutter) discloses a method for imparting thermal stability to a protein composition in the presence of a polyol.

EP 381 345 (Corint) discloses an aqueous liquid of a peptide, desmopressin, in the presence of carboxymethyl-cellulose.

In WO 89/09614 (Genentech), a stabilized formulation of human growth hormone containing glycine, mannitol, optionally a non-ionic surfactant and a buffer at pH 4–8 is disclosed. The non-ionic surfactant is added for reduced aggregation and denaturation. The formulation has an increased stability in lyophilized form and as a solution obtained after reconstitution.

EP 303 746 (International Minerals and Chemical corporation) discloses growth hormone (GH) stabilized in aqueous environment by mixing the growth hormone with polyol, amino acid, polymer of amino acid or choline derivative.

U.S.Pat. No. 4,165,370 (Coval) discloses a gamma globulin solution and a process for the preparation thereof. The solutions contains polyethylene glycol (PEG).

In EP 77 870 (Green Cross) the addition of amino acids, monosaccarides, oligosaccarides or sugar alcohols or hydrocarbon carboxylic acid to improve stability of a solution containing factor VIII is disclosed.

EP 440 989 (FUJISAWA) discloses a method for preparing a dried composition of IGF-1, which comprises drying a solution containing IGF-1 together with a strong acid.

IGF-1 in a citrate buffer at pH 6 is known from WO 91/18621, Genentech. Nothing is mentioned regarding stability of IGF-1.

Proteins are different with regard to physiological properties. When preparing a pharmaceutical preparation which should be physiologically acceptable, and stable for a long time, consideration can not only be taken to the physiological properties of the protein but also other aspects must be considered such as the industrial manufacture, easy handling for the patient and safety for the patient. The results of these aspects are not predictable when testing different formulations and each protein has often a unique solution regarding stability.

It would facilitate the use of IGF-1 if the protein could be produced and distributed as a solution to the patient, who could inject the medicament directly without reconstitution. The solution must be stable for at least two years and it would be advantageous if the final pharmaceutical solution only contained a minimum of additives, such as sugars, tensides etc.

For solutions intended for subcutaneous injection, pain can be a problem, especially if the pH of the solution deviates from the physiological pH. For stability reason of the active substance it can still be necessary to choose a pH deviating from the physiological pH. For such solution, a mean to overcome the pain upon injection would be most important, especially of the drug is to be injected regularly for many years, e.g. IGF-1.

pH is of importance and normally a pH 7 is chosen for solutions to be injected, as this is the physiological pH. Subcutaneous injections of preparations with pH 6 often induce pain. It is known (J. C. Fleishaker et al. J Clin Pharmacol 1 993:33; 182–190) that a saline solution give less pain that citrate buffer or a citrate buffer containing a drug (here Tiralazad Mesylate). L. A. M. Frenken et al. in BMJ Vol 303, 3 Aug. 1991, reported a study which showed that EPO in a buffer of albumin and citrate, gave more pain that EPO in phosphate buffer of the same pH.

The problem to find a stable solution for IGF-1 which does not hurt when injected has not until now been resolved.

It has now been found that the pain is significantly reduced when a solution according to the invention is used. It is in fact so, that the pain felt is the same as when an isotonic aqueous sodium chloride solution is injected subcutaneously.

We have thus found a new formulation which solves the above mentioned problems.

We have found that the stability for IGF-1 in solution is not so good at pH 7 but that pH 6 gives a better stability. For storage at room temperature, the choice of pH is more important than at 5° C. and pH must be less than 7.

We have also found that he stability when using citrate or phosphate as buffer is the same. Compare examples 5 and 6. In our pain study (Example 10) is shown that pH 7 gives less pain (as expected), but our stability studies show that the stability is not good enough at pH 7. By using pH 6 and a low amount of buffer (below 50 mmol) the pain is as low as when using pH 7. This is a surprising finding.

As it is known that citrate buffer can give pain when injected, we have chosen phosphate as the preferred buffer and thereby found a new composition which is stable at 5° C. for 24 months and which does not give pain to the patient and which has a better stability at 30° C. than expected.

A stable solution of IGF-1, only containing a buffer and a salt for providing isotonicity is not known and it must be regarded as surprising, when studying the prior art, that such a solution is stable for two years without any other additional components and also well tolerated by the patient.

Figure 1B:
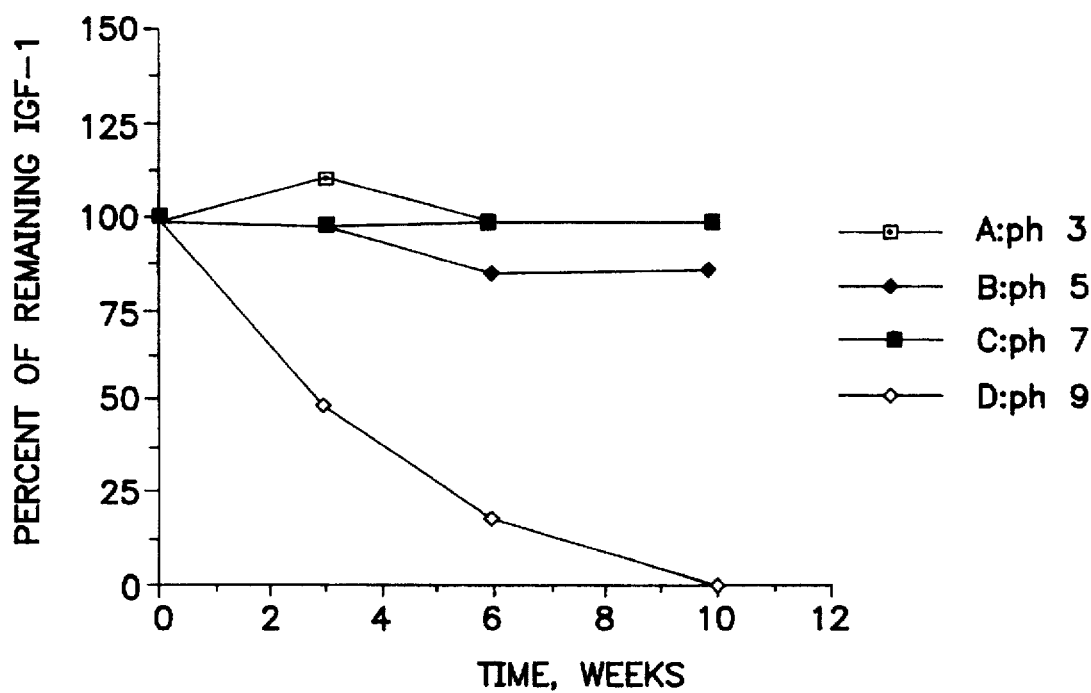

The following figures are annexed:

FIG. 1a and 1b. Percentage of remaining concentration of IGF-1 at different pH after storage at 5° C. and 30° C., respectively during 10 weeks storage. Ex 3

Figure 2A:
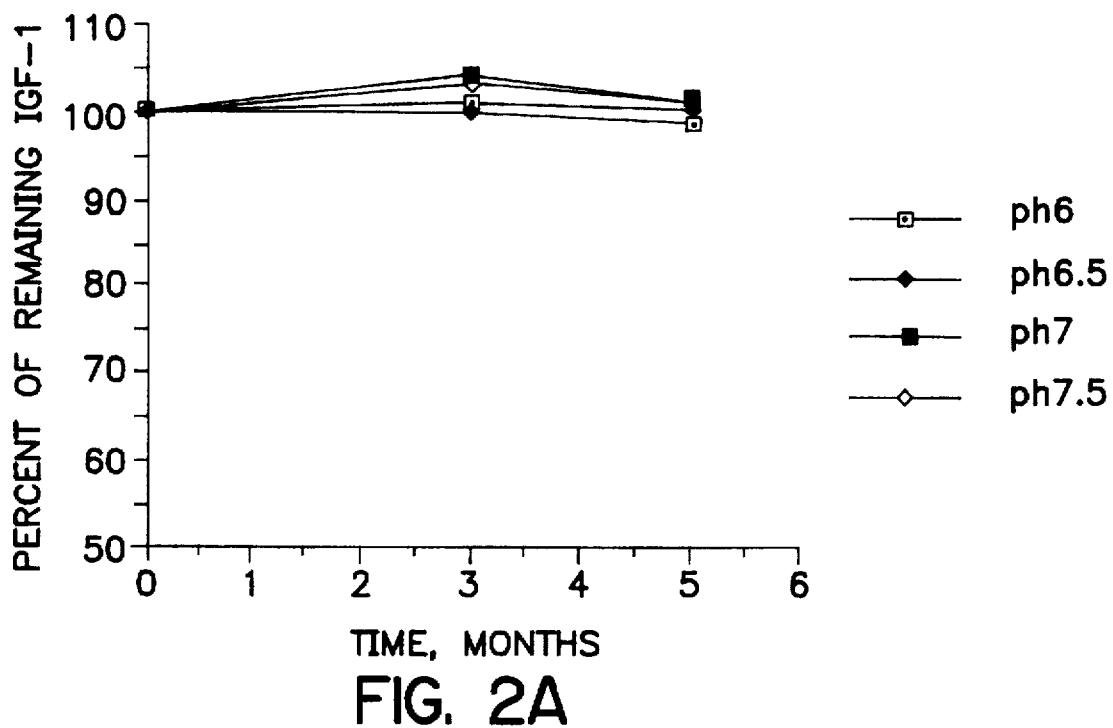
Figure 2B:
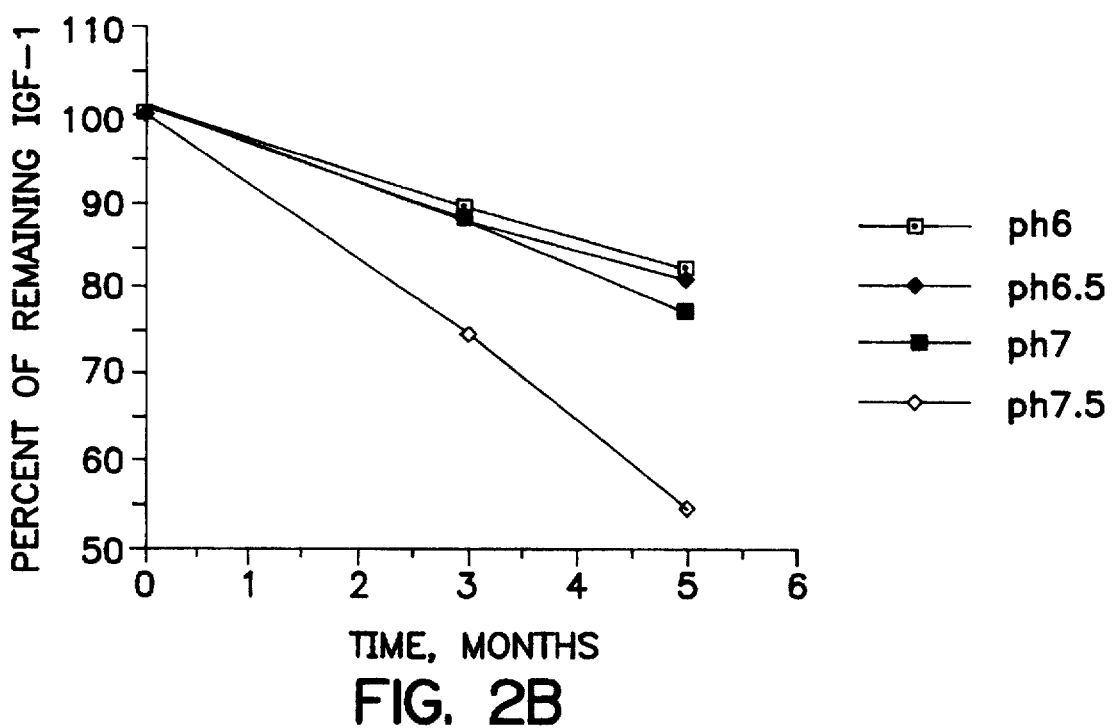

FIG. 2a and 2b. Percentage of remaining concentration of IGF-1 at different pH after storage at 5° C. and 30° C., respectively during 5 months storage. Ex 4

THE INVENTION

The invention relates to a stable solution containing IGF-1 or any functional analogue thereof and a phosphate buffer in an amount of 50 mmol or less, giving a pH of 5.5 to 6.5 , preferably 5.7–6.2 in an isotonic solution for injection.

The claimed solution in which the amount of phosphate buffer is 5–20 mmol/L, preferably around 10 mmol/L gives a reduced pain upon subcutaneous injection in comparison to a composition comprising a higher amount of phosphate.

The claimed solution has a remaining activity of at least 90% of its residual original value after +5±3° C. storage for at least 24 months.

The solution could contain IGF-1, a buffer and an isotonic agent and optionally a preservative. There is thus no need for other stabilizing agents.

The amount of the phosphate buffer is normally in an amount of 5–50 mmol/L, preferably 5–20 mmol/L and more preferably around 10 mmol/L.

The solution has preferably 10 mmol/L sodium phosphate buffer and the pH is 5.7–6.2.

The solution should be isotonic, which could easily be made by any of several excipients known for a person skilled in the art. E.g. NaCl, glycin, mannitol, glycerol and/or other carbohydrates can be added. Benzyl alcohol could be chosen as preservative.

The invention also relates to a process for preparation of the formulation by mixing IGF-1 or any functional analogue thereof with a phosphate buffer substance providing a pH of 5.5 to 6.5 and an isotonic agent and optionally a preservative. It also relates to a method for treatment of a patient in need of IGF-1 or any functional analogue thereof by administering the claimed formulation.

By Insulin-like Growth Factor (IGF-1) is meant both naturally occurring human and animal IGF-1 and recombinant IGF-1 (rIGF-1), such as rhIGF-1 (human), rbIGF-1 (bovine) and rpIGF-1 (porcine). By functional analogues are meant compounds having the same therapeutic effect as IGF-1 in animals and humans.

The concentration of IGF-1 is only dependent of its solubility in the used buffer and the desired therapeutically amount for the given dose. Preferably the concentration of IGF-1 is 1–100 mg/ml and more preferably 1–20 mg/ml.

EXAMPLES

The recombinant human IGF-1 (rhIGF-1) used in the experiments was produced in yeast. rhIGF-1 was initially synthesised as a hybrid protein fused to the yeast a α-mating factor pre-pro leader peptide. After expression the primary translation product was secreted out of the cell. During this process the pre-pro-leader was cleaved off. Correctly processed and secreted rhIGF-I could then be isolated from the fermentation media in its native form.

The media with rhIGF-1 was then micro filtered and impurities were removed by several chromatographic techniques known within the field.

All buffer components used in the examples fulfil the requirements prescribed in Ph. Eur. 2nd Ed.

In the examples 1, 2, 5 and 8 lyophilized IGF-1 pools from the final step in the purification process were dissolved in the formulation buffer and chromatographed on a Sephadex G-50 column.

In the examples 3 and 4 lyophilized IGF-1 pools from the final step in the purification process were dissolved in the formulation buffer.

In the examples 6, 7 and 9 solutions of IGF-1 pools from the final step in the purification process were ultrafiltered to obtain a correct concentration and the correct buffer formulation.

The samples were stored at +5±3° C. or +30±3° C.

The following analytical techniques were used in all examples:

Reversed Phase HPLC (RP-HPLC) The elution system is composed of acetonitrile, water, phosphate buffer and propane sulphonic acid sodium salt. Elution is accomplished by decreasing the polarity of the mobile phase. UV detection at 220 nm. Used for measurement of concentration and purity of IGF-1.

SDS-PAGE. Protein preparations of IGF-1 were denaturated by sodium dodecyl sulphate (SDS) to yield negatively charged complexes of protein-SDS. The samples were reduced with 2-mercaptoethanol. Separation was obtained according to molecular size by electrophoresis in polyacrylamide gels (PAGE) in the presence of SDS. After electrophoresis the proteins in the gel were fixed and stained with silver. The evaluation of the gel was done semi-quantitively and qualitatively by comparing the samples with standards and reference. Used for detection of IGF-1 dimers, polymers or fragments.

RRA. Radioreceptorassay is carried out essentially according to K Hall et al, J. Clin. Endocrin. Metab. 39, 973–76 (1974). Crude membrane fractions were prepared from human placenta. Incubation is performed at +4° C. After incubation RRA buffer is added to tubes which are centrifuged. All tubes are counted in a gamma counter. Bound/total radioactivity is calculated, as well as bound/total bound radioactivity. The standard curve is drawn and the concentration of IGF-1 in the unknown samples is calculated.

pH was carried out as prescribed in Ph. Eur. 2nd Ed.

The reference samples formulations for examples 3 and 4 were stored at −70° C. and thawed when the analyses were performed.

Example 1.

This example presents the results from a stability study of a solution which has been stored at +5° and +30° C. Composition per mL:

| IGF-I | 1 mg |
|---|---|
| Sodium dihydrogen phosphate | 5.25 mg |
| Disodium phosphate | 0.89 mg |
| Sodium chloride | 6.43 mg |
| Water for injection | to make 1.0 ml |
| pH | 5.9 |

This composition gives a concentration of 1 mg/mL IGF-1 in 50 mmol/L sodium phosphate buffer, and a pH 6, with 10 mmol/L sodium chloride as tonicity adjuster. 4 mL of this solution was filled in a sterile 5 mL glass ampoule.

All samples were stored protected from light and investigated after 12, and 24 months at +5 +/−3° C. and after 3, and 12 months at +30 +/−3° C.

RESULTS. The results after storage at +5 and +30° C. are presented in tables 1a and 1b respectively.

TABLE 1a

| 1 mg/ml IGF-I stored at +5° C. | | | |
|---|---|---|---|
| TIME months | RP-HPLC mg/ml | RP-HPLC % of orig. conc. | RP-HPLC purity % |
| 0 | 0.99 | | 99.0 |
| 12 | 0.94 | 95 | 97.6 |
| 24 | 0.93 | 94 | 97.7 |

TABLE 1b

| 1 mg/ml IGF-I stored at +30° C. | | | |
|---|---|---|---|
| TIME months | RP-HPLC mg/ml | RP-HPLC % of orig. conc. | RP-HPLC purity % |
| 0 | 0.99 | | 99.0 |
| 3 | 0.85 | 86 | 88.5 |
| 12 | 0.68 | 69 | 72.4 |

RP-HPLC

After 24 months of storage at +5° C. 94% of the original concentration remained.

At +30° C. 86% of IGF-1 remained after 3 months.

Conclusion

This study shows that storage at +5° C. for 24 months does not largely influence the quality of the product.

Example 2

The purpose of this study was to compare the stability of IGF-1 formulated in an aqueous solution with 10 or 50 mmol/L phosphate buffer, pH 6.

| Composition 2A: | |
|---|---|
| 1 mL contains: | |
| IGF-I | 2 mg |
| Sodium dihydrogen phosphate | 5.25 mg |
| Disodium phosphate | 0.89 mg |
| Sodium chloride | 6.43 mg |
| Water for injection | to make 1.0 ml |
| pH | 5.9 |

The concentration of the buffer is 50 mmol/L.

| Composition 2B: | |
|---|---|
| 1 ml contains: | |
| IGF-I | 1.7 mg |
| Sodium dihydrogen phosphate | 1.02 mg |
| Disodium phosphate | 0.21 mg |
| Sodium chloride | 8.48 mg |
| Water for injection | to make 1.0 ml |
| pH | 6.0 |

The concentration of the buffer is 10 mmol/L.

RESULTS

The results of analysis of IGF-1 in the formulation with 50 mmol/L phosphate buffer are presented in tables 2a–b and the results for IGF-1 in 10 mmol/L phosphate in tables 2c–d.

TABLE 2a

| Composition 2A stored at +5° C. | | | |
|---|---|---|---|
| TIME months | RP-HPLC mg/ml | RP-HPLC % of orig. conc. | RP-HPLC purity % |
| 0 | 2.1 | — | 99.8 |
| 12 | 2.0 | 95 | 98.5 |
| 24 | 2.0 | 95 | 97.8 |

TABLE 2b

Composition 2A stored at +30° C.

| TIME months | RP-HPLC mg/ml | RP-HPLC % of orig. conc. | RP-HPLC purity % |
|---|---|---|---|
| 0 | 2.1 | | 99.8 |
| 3 | 1.8 | 86 | 88.0 |
| 9 | 1.4 | 67 | 73.5 |

TABLE 2c

Composition 2B stored at +5° C.

| TIME months | RP-HPLC mg/ml | RP-HPLC % of orig. conc. | RP-HPLC purity % |
|---|---|---|---|
| 0 | 1.7 | | 99.6 |
| 12 | 1.7 | 100 | 98.2 |
| 24 | 1.7 | 100 | 97.7 |

TABLE 2d

Composition 2B stored at +30° C.

| TIME months | RP-HPLC mg/ml | RP-HPLC % of orig. conc. | RP-HPLC purity % |
|---|---|---|---|
| 0 | 1.7 | | 99.6 |
| 3 | 1.5 | 88 | 87.7 |
| 9 | 1.2 | 71 | 73.9 |

From the data in the tables it can be noted that there were no significant differences in stability of IGF-1 in the two investigated formulations.

Analysis by SDS-PAGE could not detect any differences in stability between the two formulations.

The buffer capacity of a 10 mmol/L phosphate buffer has proven to be sufficient to maintain a stable pH of the formulation.

New clinical data has indicated that a phosphate buffer concentration of 10 mmol/L would be tolerated better by patients receiving subcutaneous injections.

Conclusion

The stability of IGF-1 2 mg/ml formulated in 10 mmol/L phosphate buffer, pH 6, is the same as in 50 mmol/L phosphate buffer.

IGF-1 2 mg/ml formulated in 10 mmol/L phosphate buffer, pH 6, was found to be stable for 24 months when stored at +5+3° C.

Example 3

The purpose of this experiment was to study the influence of pH on the stability of IGF-1 in simple buffer solutions. Pharmaceutical use of IGF-1 necessitates isotonic solutions, and sodium chloride was chosen as the tonicity agent. A wide pH range was chosen for this experiment, partly to provoke changes at the extreme ends (pH 3 and 9) and partly to cover the pharmacological pH range, in this case pH 5 and 7.

For comparison, IGF-1 in the same buffer solutions but without sodium chloride were included in this study. E–H are thus not isotonic. The reason for this was to investigate if the sodium chloride affected the stability of IGF-1.

Experimental Method

Solutions containing 750 μg/ml of IGF-1 were preparared in the following buffers:

| A: | 50 mmol/L sodium citrate | pH = 3 |
|---|---|---|
| | 95 mmol/L sodium chloride | |
| B: | 50 mmol/L sodium acetate | pH = 5 |
| | 95 mmol/L sodium chloride | |
| C: | 50 mmol/L sodium phosphate | pH = 7 |
| | 95 mmol/L sodium chloride | |
| D: | 50 mmol/L glycin | pH = 9 |
| | 95 mmol/L sodium chloride | |
| E: | 50 mmol/L sodium citrate | pH = 3 |
| F: | 50 mmol/L sodium acetate | pH = 5 |
| G: | 50 mmol/L sodium phosphate | pH = 7 |
| H: | 50 mmol/L glycinE | pH = 9 |

Storage: 0 (initial samples), 3, 6 and 10 weeks (samples A–D) or 0 and 10 weeks (samples E–H).

Temperature: +5° C. and +30° C.

Results

RP-HPLC gave the results as given in FIGS. 1a and 1b. in which the result for A, B, C and D at +5° C. and +30° C. are shown and calculated as percentage. Similar results were obtained for solutions E–H.

The concentration and RRA activity of IGF-1 in the buffers with sodium chloride at pH 3, 5 and 7 were stable up to 10 weeks at +5° C. At +30° C., the concentration of IGF-1 in glycine buffer (pH=9) was not stable when analyzed after three weeks. At pH 3, 5 and 7 in the buffers with sodium chloride, the concentration and RRA activity of IGF-1 was slightly diminished when stored for 10 weeks at +30° C. At pH 9, and stored for 10 weeks at +30° C., the IGF-1 concentration, receptor activity and immunological activity were greatly reduced. The solutions without sodium chloride were slightly less stable than their isotonic counterparts, according to HPLC, and comparably stable according to RRA.

SDS-PAGE

Changes in the molecular size distribution occured when IGF-1 in buffers A and D (pH 3 and 9 respectively) were stored for 3 weeks at +30° C. but there were no changes in buffers B and C (pH 5 and 7 respectively).

CONCLUSION

The results of this experiment shows that IGF-1 is more stable in sodium acetate buffer, pH 5 and in sodium phosphate buffer, pH 7, than in sodium citrate buffer pH 3 or glycine buffer, pH 9. Also, the results indicate that the presence of sodium chloride has a slightly positive effect on the stability of IGF-1 in these buffer solutions.

Example 4

According to the results of the study in example 3, IGF-1 was more stable at pH 5 and 7 than at pH 3 and 9. Because formulations with a pH as low as pH 5 may cause discomfort when administered subcutaneously or intramuscularly, a pH above 5 should be prefered and the pH range chosen for this experiment was pH 6 to pH 7.5.

Solutions of sodium dihydrogen phosphate have buffering capacity in this range and are suitable for parenteral injection when made isotonic. For this reason, sodium phosphate, with addition of either NaCl or glycerol to raise the tonicity, was the buffer used in this study.

The purpose of this preformulation study was to determine if there is an optimal pH for the formulation of IGF-1 to make an assessment of the stability of IGF-1 in these solutions.

Experimental Method

Freeze dried IGF-1 bulk was dissolved in each of five buffer solutions to a concentration of about 1 mg IGF-1/ml. The buffer solutions were prepared from sodium dihydrogen phosphate and disodium phosphate proportionately to make 50 mmol/L, pH 6, 6.5, 7 and 7.5. Sodium chloride, 100 mmol/L was added to four of the solutions (pH 6–7.5) as a tonicity agent to bring the osmolality to about 290 mmol/L. For comparison glycerol, 200 mmol/L was added instead of sodium chloride to a pH 7 solution. The individual buffer compositions are listed in table 3. The volume of each solution was 125 ml. The five IGF-1 solutions were each filtered through a sterile Durapore® filter (Millipore, 47 mm diam., 0.22 µm pore size) and dispensed using a peristaltic pump, (Schuco Peristaltic Filler, Paxall Schubert Machinery Co. A/S) into sterile glass vials to a volume of 1 ml/vial. The vials were stoppered with sterile rubber stoppers and sealed with metal caps. The filled vials were subsequently stored and analyzed.

TABLE 3

Composition per vial and pH of each IGF-I

| Solution: labelled DsQ 12 | A | B | C | D | E |
|---|---|---|---|---|---|
| Ingredient | | | | | |
| IGF-I (freeze-dried powder) | 1 mg | 1 mg | 1 mg | 1 mg | 1 mg |
| Disodium phosphate, dodecahydrate | 2.2 mg | 5.6 mg | 10.9 mg | 15.0 mg | 10.9 mg |
| Sodium dihydrogen phosphate, monohydrate | 6.0 mg | 4.7 mg | 0.3 mg | 0.1 mg | 0.3 mg |
| Sodium chloride (solutions A–D) | 5.8 mg | 5.8 mg | 5.8 mg | 5.8 mg | — |
| Glycerol | — | — | — | — | 18.4 mg |
| Water for injection to make | 1 ml | 1 ml | 1 ml | 1 ml | 1 ml |
| pH: | 6 | 6.5 | 7 | 7.5 | 7 |

RESULTS

The results are shown in FIGS. 2a and 2b giving percent of reference value for IGF-1 according to RP-HPLC. According to the results, at +30° C., IGF-1 in sodium phosphate buffer with NaCl is stable at pH 6 and somewhat less stable at pH 6.5 and 7, and much less stable at pH 7.5. Also, the addition of glycerol instead of NaCl decreased the stability of IGF-1.

Conclusion

In this experiment two conclusions can be made. Firstly, in the range of pH 6 to pH 7.5, IGF-1 in isotonic sodium phosphate buffer (with NaCl as tonicity agent) is more stable the lower the pH, i.e. stability decreases with higher pH. Secondly, IGF-1 in this isotonic sodium phosphate buffer with NaCl is stable for six months when stored at +5° C.

Example 5

The purpose of this study was to investigate the stability of IGF-1, 2 mg/ml in a citrate buffer with pH 6.

| | |
|---|---|
| IGF-I | 2 mg |
| Trisodium citrate, dihydrate | 10.5 mg |
| Disodium citrate, 1½ hydrate | 3.76 mg |
| Sodium chloride | 4.97 mg |
| Water for injection | to make 1.0 ml |
| pH | 6.0 |

The concentration of the buffer is 50 mmol/L

Results

TABLE 4

Stability data for IGF-I

| Temperature °C. | Time months | RP-HPLC concentr mg/mL | RP-HPLC purity % |
|---|---|---|---|
| +5° C. | 0 | 1.9 | 98.8 |
| | 1.5 | 2.0 | 98.0 |
| | 26 | 2.1 | 97.8 |
| 30° C. | 0 | 1.9 | 98.8 |
| | 1.5 | 1.9 | 93.6 |

Conclusion IGF-1 formulated in a citrate buffer with pH 6 was found to be stable for 26 months when stored at +5° C.

Example 6

The purpose of this study was to investigate the stability of IGF-1, 7 mg/ml in a 50 mmol/L phosphate buffer with pH 6. 1 ml contains:

| | |
|---|---|
| IGF-I | 7 mg |
| Monosodium phosphate, anhydrous | 5.25 mg |
| Disodium phosphate, anhydrous | 0.89 mg |
| Sodium chloride | 6.43 mg |
| Water for injection | to make 1.0 ml |
| pH | 5.9 |

Results

TABLE 5

Stability data for IGF-I

| Temperature °C. | Time months | RP-HPLC concentr mg/mL | RP-HPLC of orig conc. % | RP-HPLC purity % |
|---|---|---|---|---|
| 5 | 0 | 7.0 | | 99.1 |
| | 12 | 7.3 | 100 | 98.2 |
| | 18 | 7.2 | 100 | 97.4 |
| 30 | 0 | 7.0 | | 99.1 |
| | 3 | 6.2 | 89 | 94.0 |

Conclusion IGF-1 7 mg/ml was found to be stable for 18 months at +5° C. when formulated in a 50 mmol/L phosphate buffer with pH 5.9.

Example 7

The purpose of this study was to investigate the stability of IGF-1, 10 mg/ml in a 10 mmol/L phosphate buffer with pH 6. 1 mL contains:

| | |
|---|---|
| IGF-I | 10 mg |
| Monosodium phosphate, anhydrous | 1.02 mg |
| Disodium phosphate, anhydrous | 0.21 mg |
| Sodium chloride | 8.48 mg |
| Water for injection | to make 1.0 ml |
| pH | 6.0 |

Results

TABLE 6

Stability data for IGF-I

| Temperature °C. | Time months | RP-HPLC mg/mL | RP-HPLC % of orig conc % | RP-HPLC purity % |
|---|---|---|---|---|
| 5 | 0 | 10.8 | | 98.6 |
| | 12 | 10.8 | 100 | 97.8 |
| 30 | 0 | 10.8 | | 98.6 |
| | 3 | 9.4 | 92 | 86.4 |

Conclusion IGF-1 10 mg/ml was found to be stable for at least 12 months at +5° C. when formulated in a 10 mmol/L phosphate buffer with pH 6.

Example 8

The purpose of this study was to investigate the stability of IGF-1 1.4 mg/mi in a 50 mM phosphate buffer with pH 6. and benzyl alcohol as preservative.

Formulation 8a.

| Composition per ml: | |
|---|---|
| IGF-I | 1.4 mg |
| Monosodium phosphate | 5.25 mg |
| Disodium phosphate | 0.89 mg |
| Sodium chloride | 6.43 mg |
| Benzyl alcohol | 11 mg |
| Water for injection | up to 1.0 ml |
| pH | 5.9 |

A nonpreserved reference sample was also prepared, formulation 8b

The cartridges were investigated after 23 months storage at +5 +/−3° C.

The results of analysis after storage are presented in table 7

TABLE 7

2 mg/ml IGF-I stored at +5° C. for 23 months

| SAMPLE | RP-HPLC mg/ml | RP-HPLC purity % |
|---|---|---|
| Preserved, 8a | 1.4 | 98.2 |
| Unpreserved, 8b | 1.5 | 98.5 |

Conclusion

No significant differences in concentration or purity could be detected after 23 months of storage at +5° C. Benzyl alcohol does not effect the stability of IGF-1. Both formulations were stable during the studied time.

Example 9

The purpose of this study was to investigate the stability of IGF-1 9 mg/ml in a 10 mmol/L phosphate buffer with pH 6 and benzyl alcohol.

Composition per ml:

| IGF-I | 9 mg |
|---|---|
| Monosodium phosphate | 1.02 mg |
| Disodium phosphate | 0.21 mg |

| Sodium chloride | 8.48 mg |
|---|---|
| Benzylic alcohol | 14 mg |
| Water for injection | 1.0 ml |
| pH | 6.0 |

The vials were stored and investigated after 6 months at +25+/−3° C. and +5+/−3° C.

The results are presented in tables 8a and 8b

TABLE 8a 9 mg/ml IGF-I with benzyl alcohol stored at +5° C.

| TIME months | RP-HPLC mg/ml | RP-HPLC purity % |
|---|---|---|
| 0 | 8.9 | 98.4 |
| 6 | 8.8 | 98.0 |

TABLE 8b 9 mg/ml IGF-I with benzyl alcohol stored at +25° C.

| TIME months | RP-HPLC mg/mL | RP-HPLC purity % |
|---|---|---|
| 0 | 8.9 | 98.4 |
| 6 | 6.8 | 95.8 |

Conclusion

Only a small decrease in purity could be noticed after 6 months of storage at +5° C. The formulation remained stable during the study.

Example 10

The local tolerance at subcutaneous injection of 9 formulations, I-X, was investigated in 10 male subjects.

Ten injections were given on the lower arms to each subject. The injections were given with an interval of 17 minutes/inj/subject.

The total dose of rIGHF-1 was 3 mg divided into 3 injections with 1 mg IGF-1/injection.

All injections were given within 3.5 hours to each subject, with a volume of 0.2 ml/injection.

A sodium chloride composition with physiological pH, composition 1, was used as a control.

The injection pain, assessed by the volunteers on a horizontal visual analogue scale (V.A.S.) 0–100 mm, 30 seconds after each injection ( 0 mm means no pain, 100 mm means severe pain.

Compositions used in this study in mg
Water for injection to 1 ml

| | I | II | III | IV | V |
|---|---|---|---|---|---|
| IGF-I | — | — | — | 5.00 | — |
| Monosodium phosphate | — | 0.51 | 1.02 | 1.02 | 5.21 |
| Disodium phosphate | — | 0.11 | 0.21 | 0.21 | 0.92 |
| mmol/L phosphate | — | 5 | 10 | 10 | 50 |
| Sodium chloride | 9.0 | 8.3 | 8.48 | 8.48 | 6.3 |
| pH | 7 | 6 | 6 | 6 | 6 |

| | VI | VII | VIII | IX |
|---|---|---|---|---|
| IGF-I | 5.00 | — | — | 5.00 |
| Monosodium phosphate | 5.21 | 0.54 | 2.70 | 2.70 |

-continued

| Compositions used in this study in mg Water for injection to 1 ml | | | | |
|---|---|---|---|---|
| Disodium phosphate | 0.94 | 0.78 | 3.91 | 3.91 |
| mmol/L phosphate | 50 | 10 | 50 | 50 |
| Sodium chloride | 6.38 | 8.37 | 6.38 | 6.38 |
| pH | 6 | 7 | 7 | 7 |

When LSMEAN on V.A.S. mmol/L was calculated for each

| Composition | LSMEAN |
|---|---|
| VIII | 6.5 |
| I | 7.2 |
| IX | 8.3 |
| III | 9.7 |
| IV | 12.2 |
| II | 15.1 |
| VII | 16.3 |
| V | 30.9 |
| VI | 38.4 |

Conclusions

Compositions III and IV cause considerably less pain than compositions V and VI.

At pH 6, a decrease in buffer concentration, results in decreases discomfort at injection and reduces the injection pain to a level comparable to physiological sodium chloride solution.

This study shows that a decreased buffer concentration at pH 6 is advantageous in order to achieve the best local tolerance on injection of IGF-1.

We claim:

1. Stable solution consisting essentially of IGF-I and a phosphate buffer in an amount of 5–20 mmol giving a pH of 5.5 to 6.5 in an isotonic solution for injection and which after +5±3° C. storage for at least 24 months has a remaining activity of at least 90% of its original value.

2. Stable solution according to claim 1 in which the amount of phosphate buffer is around 10 mmol/L, and which gives a reduced pain upon subcutaneous injection in comparison to a composition comprising a higher amount of phosphate.

3. Stable solution according to claim 1 containing IGF-I, the buffer and an isotonic agent and optionally a preservative.

4. Stable solution according to any of claim 1 in which the buffer is sodium phosphate buffer.

5. Stable solution according to claim 1 which also contains NaCl.

6. Stable solution according to claim 1 which contains benzyl alcohol as preservative.

7. Stable solution according to claim 1 which also contains glycine, glycerol, mannitol and/or carbohydrates as isotonic agents.

8. A process for preparation of the stable solution according to claim 1 by mixing IGF-I with the buffer substance giving pH 5.5 to 6.5 and an isotonic agent and optionally a preservative.

9. A method for treatment of a patient in need of IGF-I by administering the stable solution according to claim 1.

10. A method for reducing local irritation and resulting pain from a subcutaneous injection of IGF-I by administering the stable solution according to claim 1.

11. Stable solution according to claim 3 in which the buffer is sodium phosphate buffer.

12. Stable solution according to claim 1 having a pH of 5.7–6.2.

13. Stable solution according to claim 1 consisting of said IGF-I as the growth hormone in said solution; and said phosphate buffer in said isotonic solution.

* * * * *